United States Patent
Yoon et al.

(10) Patent No.: US 11,109,808 B2
(45) Date of Patent: Sep. 7, 2021

(54) INTELLIGENT FITNESS AND SPORTS MOUTHGUARD

(71) Applicant: University of Florida Research Foundation, Inc., Gainesville, FL (US)

(72) Inventors: Yong Kyu Yoon, Gainesville, FL (US); Justin M. Correll, Ann Arbor, MI (US); Todd R. Schumann, Gainesville, FL (US); Sheng-Po Fang, Beaverton, OR (US); Fong Wong, Madison, WI (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 401 days.

(21) Appl. No.: 15/769,584

(22) PCT Filed: Oct. 20, 2016

(86) PCT No.: PCT/US2016/057908
§ 371 (c)(1),
(2) Date: Apr. 19, 2018

(87) PCT Pub. No.: WO2017/070343
PCT Pub. Date: Apr. 27, 2017

(65) Prior Publication Data
US 2018/0310881 A1    Nov. 1, 2018

Related U.S. Application Data (60) Provisional application No. 62/245,580, filed on Oct. 23, 2015.

(51) Int. Cl.
*A61B 5/00* (2006.01)
*A61B 5/0205* (2006.01)
(Continued)

(52) U.S. Cl.
CPC .............. *A61B 5/682* (2013.01); *A61B 5/002* (2013.01); *A61B 5/01* (2013.01); *A61B 5/021* (2013.01);
(Continued)

(58) Field of Classification Search
None
See application file for complete search history.

(56) References Cited

U.S. PATENT DOCUMENTS

| | | |
|---|---|---|
| 5,078,153 A | 1/1992 | Nordlander |
| 6,089,864 A | 7/2000 | Buckner et al. |

(Continued)

FOREIGN PATENT DOCUMENTS

| | | |
|---|---|---|
| CA | 2698078 A1 | 9/2011 |
| EP | 1245197 A2 | 10/2002 |

(Continued)

OTHER PUBLICATIONS

Kang et al. "Introduction to carbon nanotube and nanofiber smart materials" Composites Part B. Engineering vol. 37, Issue 6, 2006, pp. 382-394 (Year: 2006).*

(Continued)

*Primary Examiner* — Shirley X Jian
(74) *Attorney, Agent, or Firm* — Thomas|Horstemeyer, LLP (57) ABSTRACT

Various examples are provided for intelligent mouthguards that can be used in fitness and sport activities. In one example, an intelligent mouthguard system includes a mouthguard including sensors and an internal module in communication with the sensors. The sensors can include a nine-axis inertial sensor comprising a three-axis magnetometer, a three-axis accelerometer and a three-axis gyroscope. The three-axis magnetometer can provide a reference plane in relation to the earth's magnetic field for the three-axis (Continued)

accelerometer and the three-axis gyroscope. The internal module can provide sensor data to an external processing unit when located in an oral cavity.

20 Claims, 6 Drawing Sheets

(51) Int. Cl.
    *A61B 5/024*     (2006.01)
    *G16H 40/63*     (2018.01)
    *A61B 5/01*     (2006.01)
    *A61B 5/021*     (2006.01)
    *A61F 5/56*     (2006.01)
    *A63B 71/06*     (2006.01)
    *A63B 71/08*     (2006.01)

(52) U.S. Cl.
    CPC ...... *A61B 5/02055* (2013.01); *A61B 5/02416* (2013.01); *A61B 5/4557* (2013.01); *A61F 5/56* (2013.01); *A63B 71/0619* (2013.01); *A63B 71/085* (2013.01); *G16H 40/63* (2018.01); *A61B 5/0002* (2013.01); *A61B 5/02433* (2013.01); *A61B 2503/10* (2013.01); *A61B 2562/0214* (2013.01); *A61B 2562/0219* (2013.01); *A61B 2562/0223* (2013.01); *A61B 2562/0261* (2013.01); *A61B 2562/0285* (2013.01); *A61B 2562/06* (2013.01); *A61B 2562/12* (2013.01); *A61F 2005/563* (2013.01); *A63B 2071/065* (2013.01); *A63B 2209/00* (2013.01); *A63B 2209/02* (2013.01); *A63B 2220/18* (2013.01); *A63B 2220/40* (2013.01); *A63B 2220/44* (2013.01); *A63B 2220/53* (2013.01); *A63B 2220/56* (2013.01); *A63B 2220/805* (2013.01); *A63B 2220/89* (2013.01); *A63B 2225/50* (2013.01); *A63B 2225/52* (2013.01); *A63B 2230/00* (2013.01); *A63B 2230/06* (2013.01); *A63B 2230/50* (2013.01)

(56) References Cited

U.S. PATENT DOCUMENTS

| | | | |
|---|---|---|---|
| 6,122,961 A | 9/2000 | Geen et al. | |
| 6,638,241 B2 | 10/2003 | Yerushalmy | |
| 6,941,952 B1 | 9/2005 | Rush | |
| 7,602,301 B1* | 10/2009 | Stirling | A61B 5/1127 340/573.1 |
| 8,217,784 B2 | 7/2012 | Rastegar et al. | |
| 8,466,794 B2 | 6/2013 | Mack et al. | |
| 8,537,017 B2 | 9/2013 | Mack et al. | |
| 8,554,495 B2 | 10/2013 | Mack et al. | |
| 8,739,599 B2* | 6/2014 | Hennig | A63B 71/085 73/12.01 |
| 9,526,289 B2 | 12/2016 | Mack et al. | |
| 9,554,607 B2 | 1/2017 | Mack et al. | |
| 9,629,340 B2* | 4/2017 | Schab | G16H 40/67 |
| 9,894,885 B2* | 2/2018 | Schab | A61B 5/7282 |
| 10,517,525 B2* | 12/2019 | Yoon | A61B 5/228 |
| 2002/0094509 A1 | 7/2002 | Durbin | |
| 2004/0147237 A1 | 7/2004 | Eckl et al. | |
| 2004/0158194 A1 | 8/2004 | Wolff et al. | |
| 2005/0113654 A1 | 5/2005 | Weber et al. | |
| 2006/0166157 A1 | 7/2006 | Rahman | |
| 2006/0210951 A1 | 9/2006 | Levanoni et al. | |
| 2006/0271199 A1 | 11/2006 | Johnson | |
| 2007/0106138 A1 | 5/2007 | Beiski | |
| 2007/0277836 A1* | 12/2007 | Longley | A61F 5/566 128/848 |
| 2009/0210032 A1 | 8/2009 | Beiski et al. | |
| 2009/0220563 A1 | 9/2009 | Shachar | |
| 2009/0237236 A1 | 9/2009 | Maassarani | |
| 2009/0303076 A1 | 12/2009 | Setiadi et al. | |
| 2011/0008744 A1 | 1/2011 | Teggatz | |
| 2011/0066066 A1 | 3/2011 | Van Kemenade et al. | |
| 2011/0179851 A1 | 7/2011 | Mack et al. | |
| 2011/0184319 A1 | 7/2011 | Mack et al. | |
| 2011/0184663 A1 | 7/2011 | Mack et al. | |
| 2011/0218455 A1* | 9/2011 | Hennig | A63B 71/085 600/553 |
| 2012/0075692 A1 | 3/2012 | Baik et al. | |
| 2012/0123225 A1 | 5/2012 | Al-Tawil | |
| 2012/0172679 A1* | 7/2012 | Logan | A61B 5/082 600/301 |
| 2012/0236895 A1 | 9/2012 | Miles | |
| 2013/0066236 A1 | 3/2013 | Herman et al. | |
| 2013/0211270 A1* | 8/2013 | St. Laurent | A61B 5/682 600/508 |
| 2014/0121792 A1* | 5/2014 | Jennings | A63B 67/002 700/91 |
| 2014/0128932 A1 | 5/2014 | Ewert et al. | |
| 2014/0187875 A1* | 7/2014 | Paris | A61B 5/6803 600/301 |
| 2014/0188010 A1* | 7/2014 | Paris | A61B 5/1126 600/595 |
| 2014/0248574 A1 | 9/2014 | Yoon et al. | |
| 2014/0275857 A1* | 9/2014 | Toth | A61M 16/021 600/301 |
| 2014/0288574 A1 | 9/2014 | Abramov | |
| 2014/0312834 A1 | 10/2014 | Tanabe et al. | |
| 2015/0080768 A1 | 3/2015 | Huang | |
| 2015/0119759 A1* | 4/2015 | Gonzales | A61B 5/1122 600/595 |
| 2015/0305671 A1 | 10/2015 | Yoon et al. | |
| 2016/0007849 A1* | 1/2016 | Krueger | A61B 3/113 600/301 |
| 2018/0153469 A1 | 6/2018 | Yoon et al. | |
| 2020/0008744 A1* | 1/2020 | Stitzel, Jr. | A63B 71/08 |

FOREIGN PATENT DOCUMENTS

| | | |
|---|---|---|
| WO | 2005115225 A2 | 12/2005 |
| WO | 2008061328 A2 | 5/2008 |
| WO | 2010092171 A2 | 8/2010 |
| WO | 2014110548 A1 | 7/2014 |
| WO | 2016183442 A1 | 11/2016 |

OTHER PUBLICATIONS

Yamada et al. "A stretchable carbon nanotube strain sensor for human-motion detection" Nature Nanotechnology vol. 6, May 2011 (Year: 2011).*

Wu et al. "Novel electrically conductive porous PDMS/Carbon nanofiber composites for deformable strain sensors and conductors" ACS Appl.Mater Interfaces Apr. 11, 2017 (Year: 2017).*

Duan et al. "Fabrication of highly stretchable conductor based on 3D printed porous poly(dimethylsiloxane) and conductive carbon nanotubes/graphene network" ACS Appl.Mater Interfaces Dec. 29, 2015 (Year: 2015).*

Sahay et al. "Electrospun composite nanofibers and their multifaceted applications" Center for Nanofibers & Nanotechnology, National University of Singapore, Singapore, Apr. 18, 2012 (Year: 2012).*

International Search Report for PCT/US2016/032353 dated Aug. 11, 2016.

International Search Report for PCT/US2014/011409 dated May 13, 2014.

Ferrari et al., "An autonomous battery-less sensor module powered by piezoelectric energy harvesting with RF transmission of multiple measurement signals", Smart Materials and Structures (2009), vol. 18 No. 8, pp. 1-9.

Martinez et al., "Polymeric Piezoelectric Sensors and Remote Communication for Detection of Bruxism", 2010 IEEE International Conference on Industrial Technology, pp. 268-273.

Makki et al., "Piezoelectric power generation for sensor applications: design of a battery-less wireless tire pressure sensor", Proc. SPIE 8066, Smart Sensors, Actuators, and MEMS V, 806618 (May 5, 2011), 11 pages.

(56) References Cited

OTHER PUBLICATIONS

Lantada et al., "Novel System for Bite-Force Sensing and Monitoring Based on Magnetic Near Field Communication", Sensors 2012, 12(9), pp. 11544-11558.

Jules Kieser et al., "Measuring Intraoral Pressure: Adaptation of a Dental Appliance Allows Measurement During Function", Dysphagia, (2008) vol. 23, No. 3, pp. 237-243.

Takahashi et al., "Effect of changes in the breathing mode and body position on tongue pressure with respiratory related oscillations", American Journal of Orthodontics and Dentofacial Orthopedics, (1999), vol. 115, No. 3, pp. 239-246.

K. Ahlberg et al., "Bruxism and sleep efficiency measured at home with wireless devices", Journal of Oral Rehabilitation, (2008) vol. 35, pp. 567-571.

Kim et al."Development of wireless bruxism monitoring device based on pressure sensitive polymer composite", Sensors and Actuators A, (2010) vol. 163, pp. 486-492.

J. Clauss et al., "In-vivo monitoring of bruxism with an intelligent tooth splint—Reliability and validity", IFMBE Proceedings, (Sep. 2009), vol. 25, No. 11, pp. 108-111.

Alvarez et al. "Diagnosis of Bruxism Based on Polymeric Piezoelectric Sensors and Remote Communication", [Online]. Available: http://www.disam.upm.es/, 6 pages.

Andres Diaz Lantada, Handbook of Active Materials for Medical Devices: Advances and Applications, Pan Stanford Publishing, Singapore, 2012, pp. 199-207.

Takeuchi et al. "A piezoelectric film based intrasplint detection method for bruxism", The Journal of Prosthetic Dentistry, (2001), vol. 86, issue 2, pp. 195-202.

Gonzalez et al., "A wearable passive force sensor powered by an active interrogator intended for intra-splint use for the detection and recording of bruxism," Pervasive Computing Technologies for Healthcare, PervasiveHealth 2009, 3rd International Conference on , pp. 1-4.

Kim et al., "Development of Bite Guard for Wireless Monitoring of Bruxism Using Pressure-Sensitive Polymer," Body Sensor Networks (BSN), 2010 International Conference on Body Sensor Networks, pp. 109-116.

Raadsheer et al., "Contribution of Jaw Muscle Size and Craniofacial Morphology to Human Bite Force Magnitude", Journal of Dental Research, (Jan. 1999), vol.78, No. 1, pp. 31-42.

No Author, mHealth New Horizons for Health Through Mobile Technologies, Global Observatory for eHealth Series, vol. 3, World Health Organization (Jun. 20, 2011), 112 pages.

Igarashi, Yoshimasa, "Analysis of the Denture Dynamics in RPD's'." 1989 Journal of Japanese Prosthdont Society, 33:369-375.

Agard et al., "Mouth guard for treating bruxism with electrostimulation," University of Wiconsin. Madison (Dec. 2001), pp. 1-27.

Humphries, Courtney, "Mouthpieces Gather Impact Data from Football Players", Mouthpieces Gather Impact Data from Football Players—MIT Technology Review (Oct. 2011), https://www.technologyreview.com/s/425724/mouthpieces-gather-impact-data-from-football-players/, pp. 1-5.

BiteStrip, up2dent, http://www.pxtpt:8080/bitestripweb/FMPro?-DB=BS_SS_CMS.fp5&-Format=bs_insert.html&-Max=1&bsss=bs&sprache=au&seitenid=home&-Find, 1 page.

International Search Report in co-pending related PCT Application PCT/US2016/57908, dated Jan. 24, 2017.

"Bluetooth Smart | Bluetooth Low Energy | BLE | Bluetooth | Bluetooth Technology Website" at Bluetooth.com, Oct. 2015. http://www.bluetooth.com/pages/Bluetooth-Smart.aspx.

"The Wearables Report: Growth trends, consumer attitudes, and why smartwatches will dominate" at Businessinsider.com, May 2015, http://www.businessinsider.com/the-wearable-computing-market-report-2014-10.

"A stretchable carbon nanotube strain sensor for human-motion detection" by T. Yamada et al., Nature Nanotechnology, vol. 6, pp. 296-301, Mar. 2011.

"Electronic-Mechanical Coupling in Graphene from in situ Nanoindentation Experiments and Multiscale Atomistic Simulations" by M. Huang, et al., Nano Letter, vol. 11, No. 3, pp. 1241-1246, Feb. 2011.

"Highly Stretchable and Sensitive Strain Sensor Based on Silver Nanowire-Elastomer Nanocomposite" by M. Amjadi, et al., ACS Nano, vol. 8, No. 5, pp. 5154-5163, Apr. 2014.

* cited by examiner

INTELLIGENT FITNESS AND SPORTS MOUTHGUARD

CROSS REFERENCE TO RELATED APPLICATIONS

This application is the 35 U.S.C. § 371 national stage application of PCT Application No. PCT/US2016/057908, filed Oct. 20, 2016, which claims priority to, and the benefit of, U.S. provisional application entitled "Intelligent Fitness and Sports Mouthguard" having Ser. No. 62/245,580, filed Oct. 23, 2015, the entireties of which are hereby incorporated by reference. This application is also related to co-pending U.S. patent application entitled "MULTIFUNCTIONAL ORAL PROSTHETIC SYSTEM" having Ser. No. 14/347,951, filed Mar. 27, 2014, the entirety of which is hereby incorporated by reference.

BACKGROUND

Concern has increased about injuries that occur during sporting activities. In particular, head traumas that can result in concussion have come under greater scrutiny. According to the US Centers for Disease Control and Prevention (CDC), more than 3.8 million sports brain injuries occur per year with 300 thousand resulting in loss of consciousness (LoC). These injuries are not limited to occurrence at the professional or collegiate level, but also include an estimated number of 250 thousand sports brain injuries occurring at the high school level. Diagnosis and treatment of such injuries can be enhanced by monitoring athletes during the sporting events.

SUMMARY

Embodiments of the present disclosure are related to intelligent mouthguards that can be used in fitness and sport activities.

In one embodiment, among others, an intelligent mouthguard system comprises a mouthguard including a nine-axis inertial sensor comprising a three-axis magnetometer, a three-axis accelerometer and a three-axis gyroscope, and an internal module in communication with the nine-axis inertial sensor. The three-axis magnetometer is configured to provide a reference plane in relation to the earth's magnetic field for the three-axis accelerometer and the three-axis gyroscope and the internal module is configured to provide sensor data corresponding to the three-axis magnetometer, the three-axis accelerometer and the three-axis gyroscope to an external processing unit when located in an oral cavity, and the external processing unit communicatively coupled to the mouthguard. In one or more aspects of these embodiments, the external processing unit can be a master device communicatively coupled to the mouthguard via a Bluetooth® link. The master device can be a smartphone. The master device can be configured to provide an indication of acceleration experienced by a wearer of the mouthguard through a user interface rendered on the master device. The master device can be configured to adjust the acceleration based upon the reference plane provided by the three-axis magnetometer.

In one or more aspects of these embodiments, the external processing unit can be a communication interface module communicatively coupled to the mouthguard and communicatively coupled to a remotely located processing device. The communication interface module can be communicatively coupled to the mouthguard via a Bluetooth® link and communicatively coupled to the remotely located processing device via a WLAN link. The internal module can be configured to transmit the sensor data from the three-axis magnetometer, the three-axis accelerometer and the three-axis gyroscope to the external processing unit. The sensor data can be transmitted to the external processing unit in real-time. The internal module can transmit the sensor data to the external processing unit from memory in response to a transmission request received from the external processing unit.

In one or more aspects of these embodiments, the intelligent mouthguard system comprises a temperature sensor. The intelligent mouthguard system comprises an infrared (IR) sensor, wherein heart rate or blood pressure can be determined based upon sensor data from the IR sensor. The intelligent mouthguard system comprises a strain gauge sensor sealed in the mouthguard. The strain gauge sensor can comprise a polydimethylsiloxane (PDMS) and carbon nanofiber (CNF) composite sensing element. The sensing element can comprise electrospun polymer derived conductive carbon nanofiber (EPD-CNF) sealed in polydimethylsiloxane (PDMS).

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Disclosed herein are various embodiments related to an intelligent mouthguard for fitness and sport activities. Reference will now be made in detail to the description of the embodiments as illustrated in the drawings, wherein like reference numbers indicate like parts throughout the several views.

In this Internet of Things (IoT) era, there is a great deal of interest in wearable devices with wireless functionality that are networked together to provide up-to-date real-time data to a central hub such as a cell phone, personal computer, or network server. The device presented here is a smart mouthguard platform with 11 sensor channels and a friendly user interface. The mouthguard platform is targeted for use in all fitness and sports activities where the user is interested in monitoring their biometric data from physical activity and their potential exposure to life threatening (head, heat, and heart related) injury. The oral cavity is a region that offers easy access and noninvasive device placement. Further, the same platform can be extended for use in bruxism monitoring and intervention. The smart mouthguard can provide real-time feedback to the user(s) or a designated official or healthcare professional. In the case of bruxism, it offers the ability to implement intervention mechanisms such as a muscle massager, heating pad and/or behavior modification through biofeedback.

The devices focus on providing a holistic approach to health monitoring by using an array of sensors to cover a complete application instead of a single sensor. For example, the sports mouthguard can implement a 9-axis inertial sensor and pressure sensors to detect dangerous force levels to which the head is subjected to, an infrared (IR) sensor for heart pulse rate and osmolality monitoring, and a temperature sensor to detect dangerous rises in core body temperature. A bruxism mouthguard can implement different sensitivity pressure sensors to detect biting force from "chattering" to clenching, an inertial sensor to detect restlessness, and a thermistor to detect rises in body temperature.

Figures 1A, 1B:
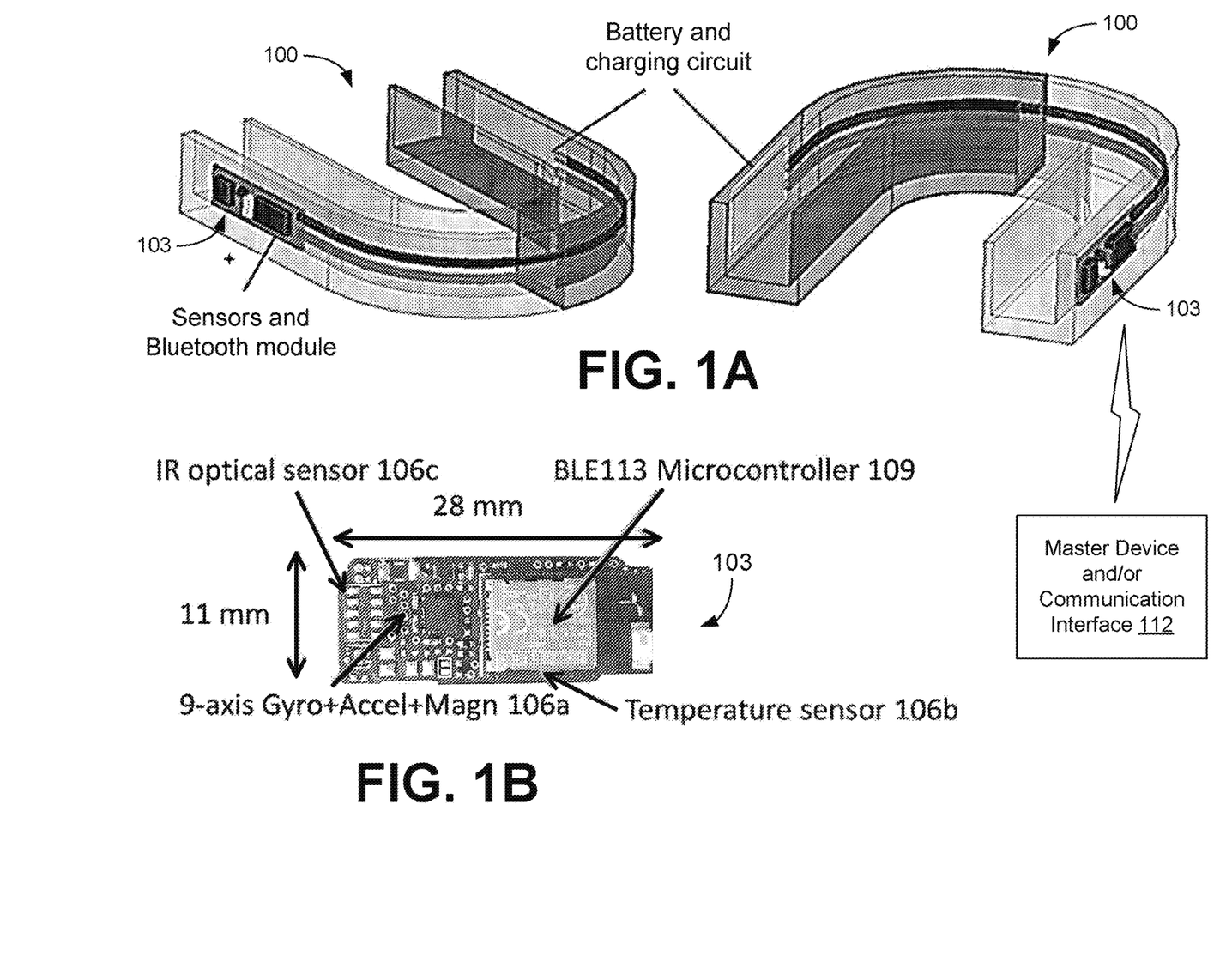
FIGS. 1A, 1B, and 1C illustrate an example of an intelligent mouthguard, in accordance with various embodiments of the present disclosure.

Referring to FIG. 1A, shown is a graphical representation illustrating an example of an intelligent mouthguard 100 including sensors, a battery, charging and wireless electronics circuitry. The intelligent mouthguard system comprises a printed circuit board 103 embedded in a mouthguard 100 and a software application that enables low-energy wireless communications (e.g., Bluetooth®, WiFi, WLAN, etc.) between the electronics in the mouthguard 100 and an external hub or server. Referring to FIG. 1B, shown is an example of the printed circuit board 103, which contains a plurality of sensors 106 (e.g., a 9-axis inertial sensor 106a, a temperature sensor 106b, an infrared (IR) optical sensor 106c, etc.) used to track user activity and/or condition. A microcontroller 109 can be configured to communicate with each of the sensors and to communicate various information to the external hub or server.

The biometric data collected from the sensor can provide the user with biometric information from physical activity and exposure to head, heat, and heart-related injuries. The software application can provide a unique user interface to interact with the mouthguard 100 and to display the acquired biometric data and injury exposure information. Further, the software application can be connected to a back-end server interface located on a remote storage device.

In the example of FIG. 1B, the printed circuit board 103 comprises an ARM Cortex microprocessor 109 with an integrated Bluetooth Low Energy (BLE) 2.4 GHz transceiver such as the Silicon Labs Blue Gecko BGM111. The Bluetooth Special Interest group outlines the communication protocol employed by BLE enabled devices as a master—peripheral relationship. In this case, the ARM Cortex BLE microprocessor 109 fulfills the peripheral role and collects the data from several sensors 106 located on the circuit board 103. The data can be transmitted to an external processing unit 112 such as a master device, e.g., a more powerful smart phone (Android or iPhone), tablet, laptop computer, or other computing device, where it can be processed and/or provided for display, or a communication interface module that can forward the data to a remotely located processing device for processing, display and/or storage. In this setup, the printed circuit board 103 maintains the smallest electrical footprint to be sufficient for integration into the mouthguard 100. This mouthguard platform provides for non-invasive and easy access to a number of biological markers and/or signals via, for example, salivary analysis.

Figure 1C:
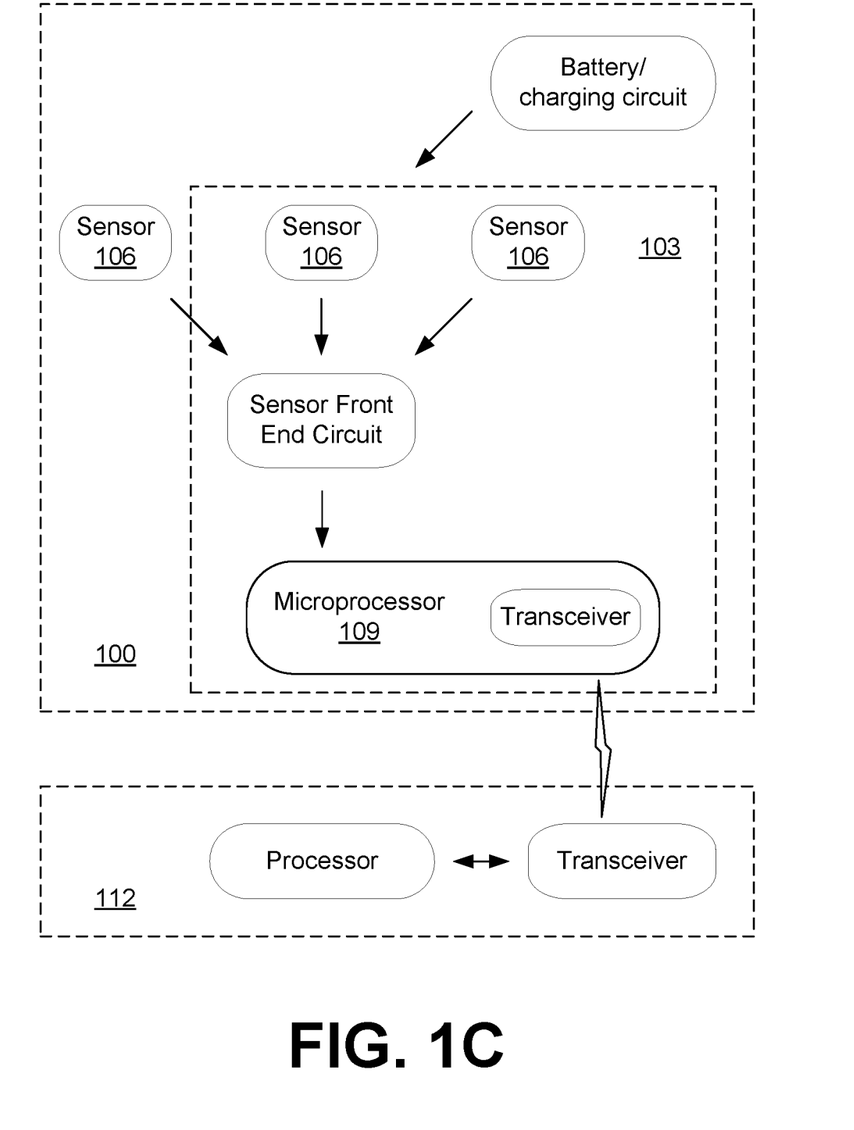

Referring next to FIG. 10, shown is an example of a sensor network of a intelligent mouthguard 100. Signals from one or more sensors 106 mounted on the printed circuit board 103 and/or in the mouthguard 100 may be received by a sensor front end circuit (e.g., a MUX/ADC) for processing by the microprocessor 109. The microprocessor 109 can provide the acquired sensor data to the master device 112 through a transceiver, which may be integrated into the microprocessor 109 or may be a separate device. The printed circuit board 103 and/or microprocessor 109 can include memory to store sensor data for subsequent transmission to the master device 112 and/or code or instructions that may be executed by the microprocessor 109. The master device 112 includes a transceiver that receives the transmitted sensor information and provides it to a processor for analysis and processing. Transmission between the mouthguard 100 and the master device 112 may be over a wireless communications link (e.g., Bluetooth®, WiFi, WLAN, etc.).

Figure 1D:
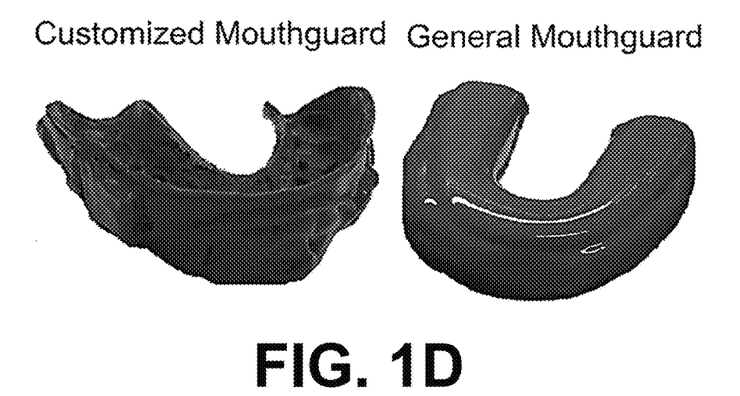
FIG. 1D includes images of examples of custom and general intelligent mouthguards, in accordance with various embodiments of the present disclosure.

The mouthguard 100 can also be referred to as the $H^3$ mouthguard as it deals with head, heat, and heart-related injuries. The mouthguard 100 is a multifunctional smart oral platform that offers real time biometric monitoring including potential danger detection and real time compliance reporting. FIG. 1D shows examples of customized and general mouthguards 100 with the printed circuit board 103, sensors, battery, and charging circuitry encased in a protective coating. The mouthguard 100 can be loaded with 11 sensor nodes which track various biomarkers such as, e.g., core body temperature, heart rate, blood pressure, and impact parameters. The system application can be extended by the addition of pressure sensors to find applications in bruxism monitoring.

9-axis Inertial Sensors. The 9-axis inertial sensor 106a of FIG. 1B can include a 3-axis accelerometer, a 3-axis gyroscope, and a 3-axis magnetometer such as in an InvenSense MPU-9250. The accelerometer can provide gravitational force data, the gyroscope can provide rotational data about an axis, and the magnetometer can provide a reference plane in relation to the earth's magnetic field. Together, the 9-axis of data can be used to create a three-dimensional (3-D) mapping of the mouthguard 100 that tracks the forces and direction of perturbations that the user experiences during physical activity. Both magnitude and direction of an impact force on the head can be detected and recorded.

Temperature Sensor. The temperature sensor 106b of FIG. 1B can be, e.g., a diode type located in the microcontroller silicon, an external low-power temperature sensor such as the Texas Instruments LM94022 multi-gain sensor, or other appropriate type of temperature sensor. The LM94022 is well suited to source the input of a sample and hold analog-to-digital converter (ADC) signals similar to the analog inputs on the Silicon Labs BGM111. The temperature sensor can be implemented to record oral temperatures, providing potential heat related injury alerts in advance. The mouthguard 100 is not limited to only analog temperature sensors but could be loaded with a digital sensor with serial output. The mouthguard 100 is not limited to a single sensor, but can use several sensors to provide a differential measurement to improve accuracy in identifying the user's core body temperature.

Heart Rate and Blood Pressure Sensor. An infrared (IR) sensor 106c such as the Silicon Labs Si1147 can be used to provide heart rate and blood pressure measurements using photoplethysmography (PPG), an optical technique that detects blood volume changes in microvascular tissues. The Si1147 comprises an IR LED and a CMOS ambient light sensor module. A portion of the infrared light projected into microvascular tissue is absorbed. Further, as the microvascular tissues expand and contract, the IR absorption changes. The ambient light sensor captures the changes and an algorithm can be used to resolve the data into a heart rate and blood pressure measurement. The IR sensor information can be used to track body condition and fitness level, which can be evaluated in real-time or stored (e.g., in the smartphone) for subsequent access.

Capacitive Pressure Sensor. The mouthguard 100 can include pressure sensors, such as capacitors with a compressible dielectric layer. As a force is applied, the effective thickness of the dielectric layer changes causing a change in capacitance. This change can be measured by detecting a change in the time constant for an RC circuit or the center frequency of an LC circuit and the relative force can be extracted. These sensors are linear for a limited range of force, and so sensors with different deflection coefficients can be used to create an array of sensors which can linearly measure the entire range of biting force for either bruxism or impact force for concussion detection.

Figure 2A:
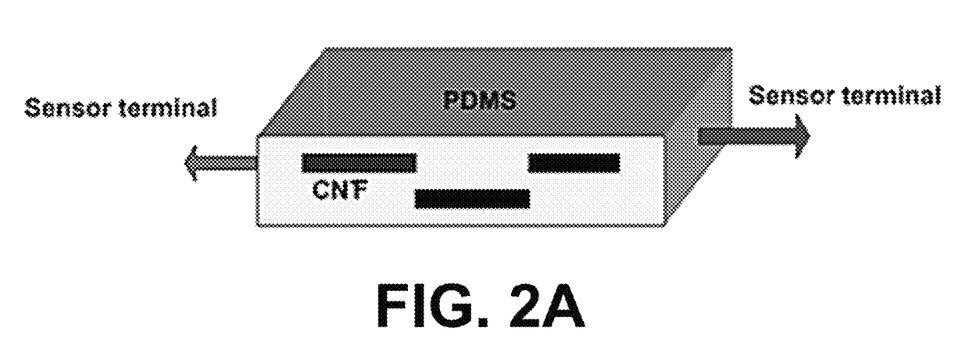
FIGS. 2A and 2B illustrate an example of a composite material strain gauge sensor, in accordance with various embodiments of the present disclosure.

Strain Gauge Pressure Sensor. The mouthguard 100 can also include a strain gauge pressure sensor, which can be used for biting force measurement. Biting during Bruxism produces a pressure of about 100 lbs to 200 lbs (or about 2000 kPa). Hence, the sensor should be able to withstand this pressure level with a reasonable resolution. For the strain gauge sensor, various options are available. For example, two options include:

A commercially available strain gauge sensor like a match stick type strain gauge, such as a pressure sensor like SCP 100 (120 kPa range) from VTI technologies, and pressure membrane.
  An engineered composite material made of polydimethylsiloxane (PDMS) and carbon nanofiber (CNF) considering size constraints and biocompatibility issues is used. FIG. 2A is a schematic diagram illustrating the PDMS/CNF sensor and FIG. 2B is an image showing a fabricated PDMS/CNF sensor.

Figure 2B:
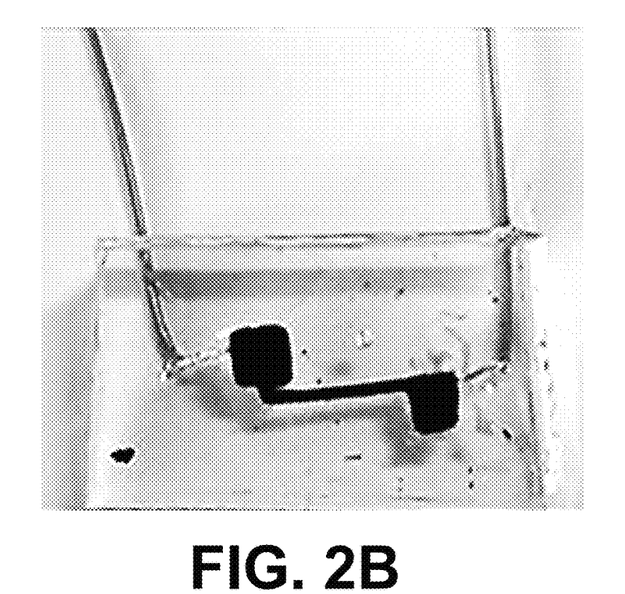

In some implementations, the PDMS/CNF sensor or FIG. 2B can be made of electrospun polymer (e.g., SU-8) derived conductive carbon nanofiber (EPD-CNF) and PDMS. This EPD-CNF/PDMS composite exhibits strong piezoresistivity that translates into excellent sensitivity with an extremely high gauge factor of 23.1, which is about 12-30 times higher than produced by graphene nanoribbon or carbon nanotube based nanocomposite sensors. The EPD-CNF/PDMS composite offers a low cost, high sensitivity sensor that can be manufactured and incorporated into the mouthguard 100. The composite remains intact under high mechanical strain, such as occurs during use, which may be attributed to the continuous and tangled electrospun nanofibers in the sensor. The strain sensor can be embedded in a side or bottom surface of the mouthguard 100 and communicatively coupled to the microprocessor 109 on the printed circuit board 103.

Figure 2C:
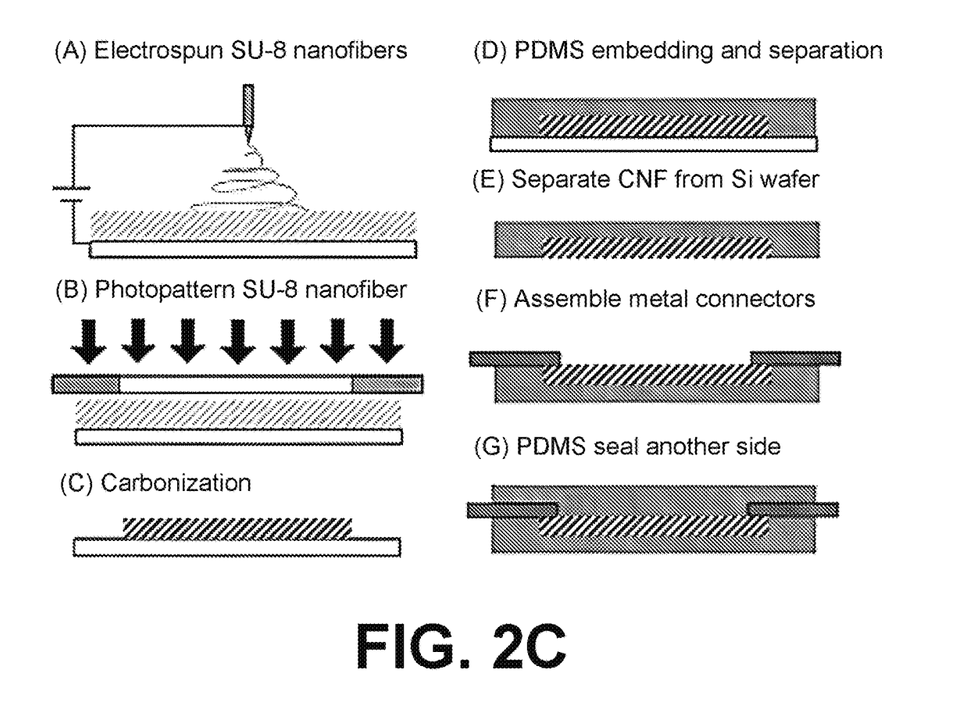
FIG. 2C illustrates an example of fabrication of a strain gauge sensor using electrospun polymer derived conductive carbon nanofiber (EPD-CNF) and polydimethylsiloxane (PDMS), in accordance with various embodiments of the present disclosure.
Figure 2D:
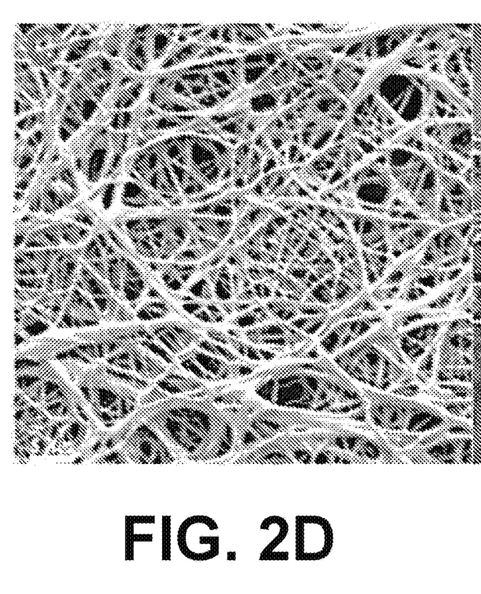
FIGS. 2D and 2E are images of the carbon nanofiber embedded in the PDMS, in accordance with various embodiments of the present disclosure.
Figure 2E:
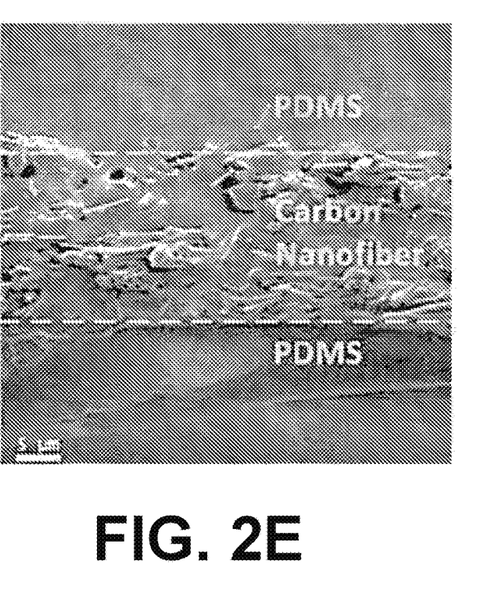

FIG. 2C illustrates an example of the fabrication of the composite sensor. Initially, SU-8 nanofibers can be electrospun (A) on a silicon (Si) wafer and patterned (B) using photolithography. Men deposited, the electrospun nanofibers form a continuous and randomly oriented layer that form a microscale spring. Carbonization (C) of the electrospun nanofibers enables the formation of stretchable conductive EPD-CNF within the embedding elastomers. The EPD-CNF can then be partially embedded (D) in PDMS and separated (E) from the Si wafer. Connectors can be assembled (F) on the EPD-CNF, which are then sealed (G) in PDMS as shown. FIG. 2D is a scanning electron microscope (SEM) image of carbonized nanofibers and FIG. 2E shows a cross-sectional view of the EPD-CNF embedded within the PDMS.

Figure 2F:
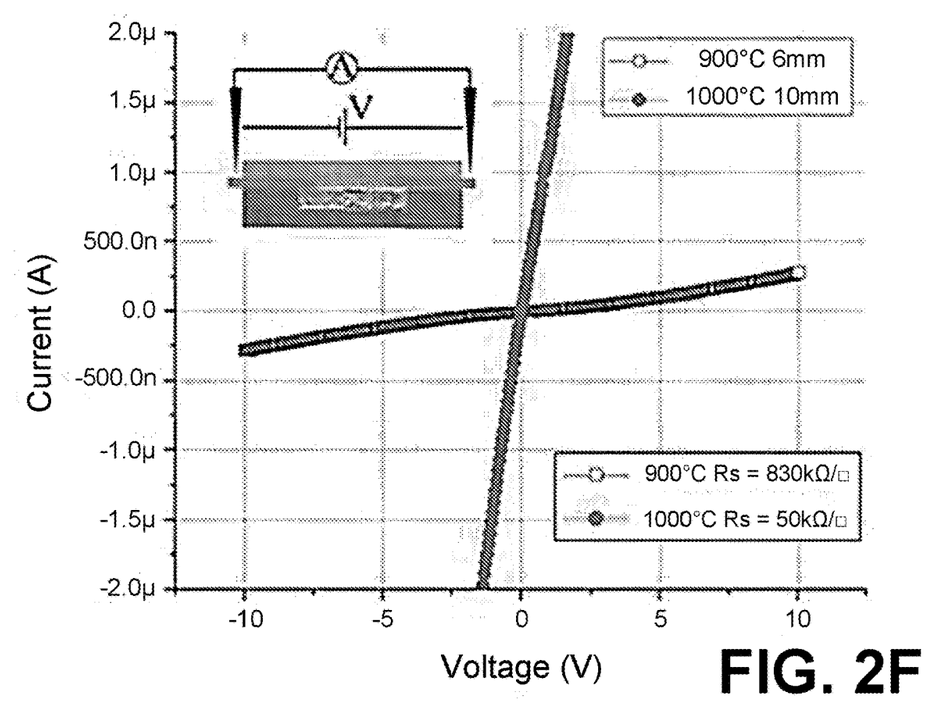
FIGS. 2F and 2G illustrate test results of the EPD-CNF/PDMS stain sensor, in accordance with various embodiments of the present disclosure.
Figure 2G:
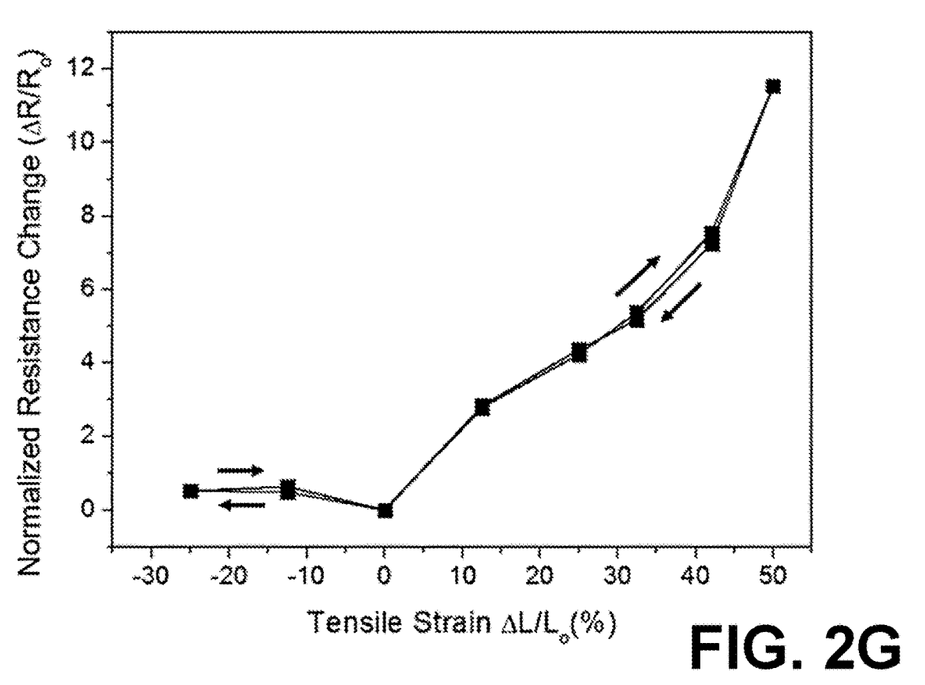

FIG. 2F shows the measured current-voltage (I-V) curves for strain sensors of FIG. 2B including EPD-CNFs that were carbonized at 900° C. and 1000° C. The measuring setup is shown in inset of FIG. 2F. The extracted sheet resistances (Rs) of those carbonized nanofibers at 900° C. and 1000° C. were 830 kΩ/□ and 50 kΩ/□, respectively, where Ω/□ is ohms per square. FIG. 2G shows a measured gauge factor $$\left(GF = \frac{\Delta R}{R} \middle/ \epsilon\right)$$

of 23.1 with 50% strain at room temperature. The strain range can be further improved by optimizing the PDMS thickness.

Wireless Power Delivery. As shown in FIG. 1A, the mouthguard 100 can include a battery and charging circuit for wireless power delivery to the circuit board 103. Power can be delivered between a transmitter and a receiver located in the mouthguard 100 by inductive coupling between the antennas 809. The charging circuit can be part of a wireless power delivery system configured to supply power to the battery through inductive coupling. The delivered power may then be regulated by the charging circuit for delivery to loads on the circuit board 103 and/or sensors in the mouthguard 100. For example, BQ500110 and BQ51013 ICs from Texas Instruments Inc. may be used as the transmitter and the receiver, respectively, with near field power coupling provided through antennas. Since the BQ500110 and BQ51013 ICs are highly integrated chips, nearly no peripherals are needed on the mouthguard 100 for power collection.

Long Distance Communication. The mouthguard 100 can be extended to support team applications. A software application deployed on a trainer's tablet (or other computing device) can communicate with and take measurements from a plurality of mouthguards 100 by pinging each individually to transfer their data to prevent channel crowding. The microcontroller 109 can transfer data to internal memory and/or external memory on the circuit board 103 during acquisition, and then transfer the stored information in response to the ping requesting transfer.

In the case of long distance transmission, the 434 MHz or 915 MHz ISM frequency bands can be used to implement a multi-layer system that includes an additional wireless module. The communication interface module 112 can either be located in the player's helmet or other equipment worn by the player, or integrated into the players clothing. Further, an external patch, which can be secured to the equipment and/or player, could be used for implementation of the communication interface module 112. The additional wireless module or communication interface 112 (external) can communicate using both 2.4 GHz (to mouthguard 100) and ISM bands (434 MHz or 915 MHz) as a virtual waypoint between the close range mouthguard 100 and externally located transceiver module located on the sideline or in coach's booth.

Figures 3A, 3B:
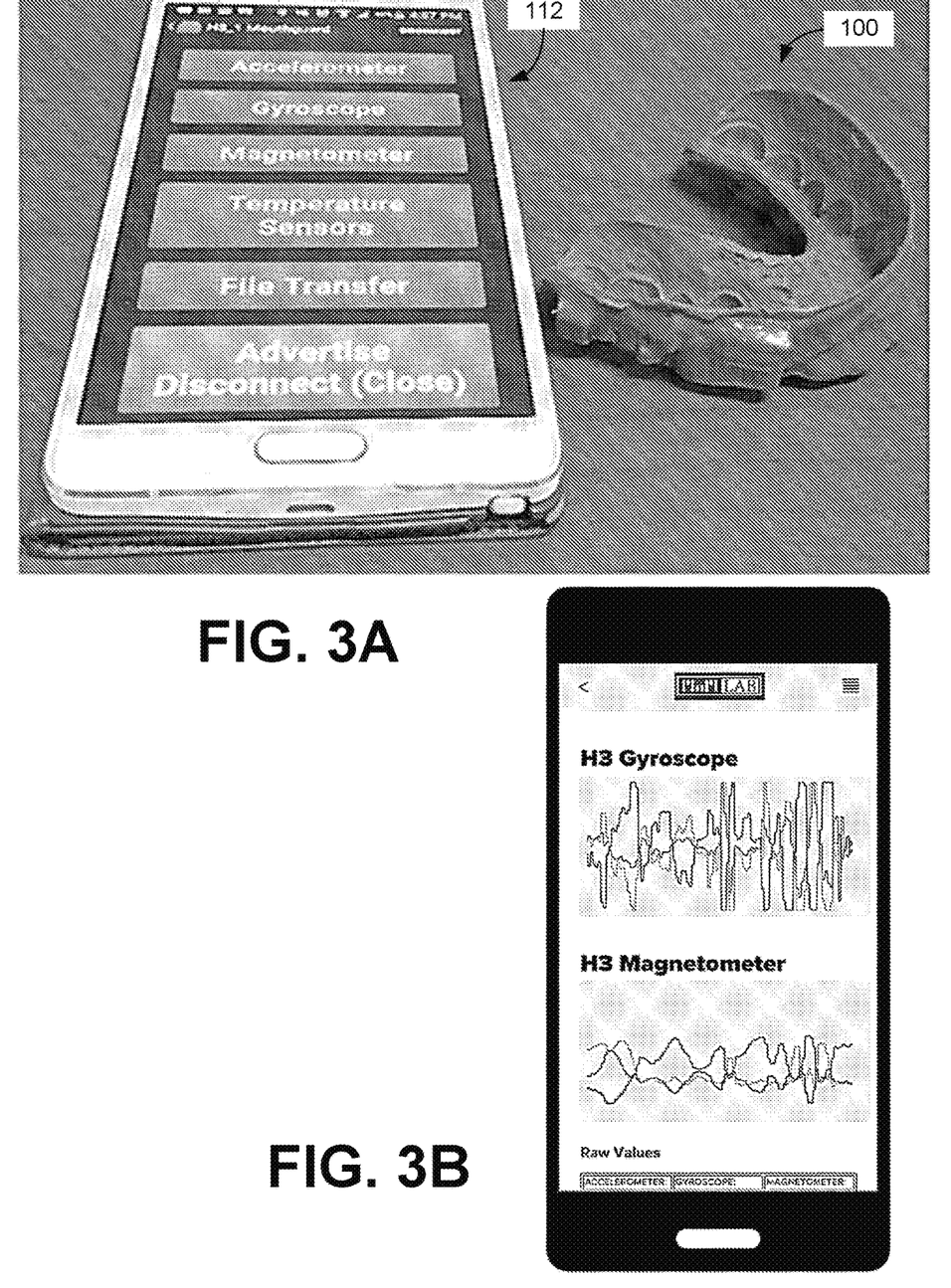
FIGS. 3A and 3B illustrate a prototype mouthguard of FIGS. 1A and 1B, and master device in communication with the mouthguard, in accordance with various embodiments of the present disclosure.

Referring to FIG. 3A, shown is an image of a prototype mouthguard 100 and a smartphone acting as the master device 112. The image shows example of an interface of the system application that is implemented on the smartphone. As shown in FIG. 3A, the interface allows a user to access the sensor information (e.g., accelerometer, gyroscope, magnetometer, temperature sensors, etc.). FIG. 3B illustrates an example of the sensor information that can be displayed on the master device. The information (e.g., biometric data) can be displayed in graphs through a user friendly mobile app for iOS or Android systems. The interface can also facilitate file transfer of the recorded sensor information from the mouthguard 100 to the master device 112 or to another externally located processing device, as described above. The interface can also allow the master device 112 to be disconnected from the mouthguard 100, allowing another device to connect as the master device.

The intelligent mouthguard 100 utilizes wearable electronics as part of a self-fitness monitoring system with wireless connectivity. Wearable electronics for fitness and wellness can help individuals monitor physical activity, diet, and sleep with continuous updates of biometric data. The mouthguard 100 can include a detection mechanism that can provide awareness of vital signs and potential sustained injury. The design and fabrication of the $H^3$ (Head, Heat, and Heart-Related) mouthguard platform with 11 sensor channels and a friendly user interface has been presented. The device can be used in all sports or fitness activities where the user is interested in their biometric data from physical activity and their potential exposure to life threatening (head) injury. The $H^3$ mouthguard platform is not limited to applications in sports fitness and wellness, but could find similar applications in the public safety (firefighter) and military sectors.

The concept can be further extended to a smart denture or retainer with a detection capability of diabetes, HIV, and cancer biomarkers from saliva and an integrated drug delivery functionality. In addition, as the mouthguard 100 is in good contact with saliva, which contains lots of biomarkers for health and disease monitoring and detection, the $H^3$ mouthguard 100 can be extended to be used as a general health monitoring and intervention tool.

The $H^3$ mouthguard 100 offers a multifunctional smart oral platform with real time biometric monitoring that includes potential danger detection and real time compliance report. The mouthguard 100 can be loaded with a plurality of sensor nodes, which track core body temperature, heart rate, blood pressure, impact parameters and/or other biometric indications. A temperature sensor 106b (FIG. 1B) can be used to measure the body temperature inside the mouth, eliminating inaccuracies found in common external wearable devices that arise from the temperature gradient between the skin and environment. An infrared sensor 106c (FIG. 1B) can be included to provide heart rate and blood pressure measurements using photoplethysmography (PPG), an optical technique that detects blood volume changes in microvascular tissues. Impact parameters can be tracked using a 9-axis inertial sensor 106a (FIG. 1B) including a 3-axis accelerometer, 3-axis gyroscope, and 3-axis magnetometer. The 3-axis magnetometer uses the earth's magnetic field to allow the sensing algorithm to compensate for drift errors over longer periods of time thus providing a more accurate measurement of impacts from a lateral force and angular momentum. The $H^3$ mouthguard 100 development includes electronics and firmware design, form factor integration, and software development. The device can provide accurate biometric analysis that can inform the user of their fitness level and exposure to risk of heat or impact related injuries. Functionalities include head impact detection (e.g., serious impact alerts and/or long term impact tracking), body temperature monitoring (e.g., potential injury alerts such as for heat stroke or dehydration), and vital sign tracking (e.g., personal fitness tracking).

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. An intelligent mouthguard system, comprising:
a mouthguard and an external processing unit;
the mouthguard including:
a nine-axis inertial sensor comprising a three-axis magnetometer, a three-axis accelerometer and a three-axis gyroscope, the three-axis magnetometer configured to provide a reference plane in relation to earth's magnetic field for the three-axis accelerometer and the three-axis gyroscope; and
an internal module in communication with the nine-axis inertial sensor, the internal module comprising a microprocessor configured to store sensor data corresponding to the three-axis magnetometer, the three-axis accelerometer and the three-axis gyroscope in a memory of the mouthguard and a transceiver configured to transmit the stored sensor data to the external processing unit when the mouthguard is located in an oral cavity, the stored sensor data transmitted in response to a transmission request received from the external processing unit communicatively coupled to the mouthguard, wherein the external processing unit is a master device communicatively coupled to the mouthguard via a low-energy wireless communications link, the master device configured to provide an indication of acceleration experienced by a wearer of the mouthguard through a user interface rendered on the master device and adjust the acceleration based upon the reference plane provided by the three-axis magnetometer.

2. The intelligent mouthguard system of claim 1, wherein the master device is a smartphone.

3. The intelligent mouthguard system of claim 1, wherein the mouthguard further comprises one of: a temperature sensor, a heart rate sensor or a blood pressure sensor.

4. An intelligent mouthguard system, comprising:
a mouthguard and an external processing unit;
the mouthguard including:
a nine-axis inertial sensor comprising a three-axis magnetometer, a three-axis accelerometer and a three-axis gyroscope, the three-axis magnetometer configured to provide a reference plane in relation to earth's magnetic field for the three-axis accelerometer and the three-axis gyroscope;
an internal module in communication with the nine-axis inertial sensor, the internal module comprising a microprocessor configured to store sensor data corresponding to the three-axis magnetometer, the three-axis accelerometer and the three-axis gyroscope in memory of the mouthguard and a transceiver configured to transmit the stored sensor data to the external processing unit when the mouthguard is located in an oral cavity, the stored sensor data transmitted in response to a transmission request received from the external processing unit communicatively coupled to the mouthguard; and
an infrared (IR) sensor, wherein blood pressure can be determined based upon sensor data from the IR sensor when the mouthguard is located in the oral cavity.

5. The intelligent mouthguard system of claim 4, wherein the external processing unit is a master device communicatively coupled to the mouthguard via a low-energy wireless communications link.

6. The intelligent mouthguard system of claim 5, wherein the master device is a smartphone.

7. The intelligent mouthguard system of claim 5, wherein the master device is configured to provide an indication of acceleration experienced by a wearer of the mouthguard through a user interface rendered on the master device.

8. The intelligent mouthguard system of claim 4, wherein the mouthguard further comprises a temperature sensor.

9. An intelligent mouthguard system, comprising:
a mouthguard and an external processing unit;
the mouthguard including:
a nine-axis inertial sensor comprising a three-axis magnetometer, a three-axis accelerometer and a three-axis gyroscope, the three-axis magnetometer configured to provide a reference plane in relation to earth's magnetic field for the three-axis accelerometer and the three-axis gyroscope;
an internal module comprising processing circuitry in communication with the nine-axis inertial sensor, the internal module configured to provide sensor data corresponding to the three-axis magnetometer, the three-axis accelerometer and the three-axis gyroscope to the external processing unit when the mouthguard is located in an oral cavity, the external processing unit communicatively coupled to the mouthguard; and
a strain gauge sensor sealed in the mouthguard, the strain gauge sensor comprising a polydimethylsiloxane (PDMS) and carbon nanofiber (CNF) composite sensing element comprising, where the sensing element comprises electrospun polymer derived conductive carbon nanofiber (EPD-CNF) sealed in the PDMS.

10. The intelligent mouthguard system of claim 9, wherein the internal module is configured to wirelessly transmit the sensor data from the three-axis magnetometer, the three-axis accelerometer and the three-axis gyroscope to the external processing unit.

11. The intelligent mouthguard system of claim 10, wherein the sensor data is transmitted to the external processing unit in real-time.

12. The intelligent mouthguard system of claim 10, wherein the internal module transmits the sensor data to the external processing unit from memory in response to a transmission request received from the external processing unit.

13. The intelligent mouthguard system of claim 9, wherein the external processing unit is configured to provide an indication of acceleration experienced by a wearer of the mouthguard through a user interface rendered on the external processing unit.

14. The intelligent mouthguard system of claim 13, wherein the external processing unit is a smartphone or tablet.

15. The intelligent mouthguard system of claim 9, wherein the mouthguard further comprises one of: a temperature sensor, a heart rate sensor or a blood pressure sensor.

16. An intelligent mouthguard system, comprising:
a mouthguard and an external processing unit,
the mouthguard including:
a nine-axis inertial sensor comprising a three-axis magnetometer, a three-axis accelerometer and a three-axis gyroscope, the three-axis magnetometer configured to provide a reference plane in relation to earth's magnetic field for the three-axis accelerometer and the three-axis gyroscope; and
an internal module in communication with the nine-axis inertial sensor, the internal module comprising a microprocessor configured to store sensor data corresponding to the three-axis magnetometer, the three-axis accelerometer and the three-axis gyroscope in memory of the mouthguard and a transceiver configured to transmit the stored sensor data to the external processing unit when the mouthguard is located in an oral cavity, the stored sensor data transmitted in response to a transmission request received from the external processing unit communicatively coupled to the mouthguard, wherein drift error in the sensor data is compensated for based upon the sensor data corresponding to the three-axis magnetometer.

17. The intelligent mouthguard system of claim 16, wherein the external processing unit is a communication interface module communicatively coupled to the mouthguard and communicatively coupled to a remotely located processing device.

18. The intelligent mouthguard system of claim 17, wherein the communication interface module is communicatively coupled to the mouthguard via a low-energy wireless communications link and communicatively coupled to the remotely located processing device via a WLAN link.

19. The intelligent mouthguard system of claim 16, further comprising a strain gauge sensor sealed in the mouthguard, and at least one of: a temperature sensor, or a blood pressure sensor.

20. The intelligent mouthguard system of claim 19, wherein the strain gauge sensor comprises a polydimethylsiloxane (PDMS) and carbon nanofiber (CNF) composite sensing element.

\* \* \* \* \*